United States Patent
Haag et al.

[11] Patent Number: 5,976,141
[45] Date of Patent: Nov. 2, 1999

[54] THREADED INSERT FOR BONE PLATE SCREW HOLE

[75] Inventors: Rene Haag, Devon; Michael H. Mackin, Exton, both of Pa.; Jeffrey W. Mast, Gross Pointe Park, Mich.; Timothy M. Chadwick, Downingtown, Pa.

[73] Assignee: Synthes (U.S.A.), Paoli, Pa.

[21] Appl. No.: 08/392,540

[22] Filed: Feb. 23, 1995

[51] Int. Cl.⁶ .................................................. A61B 17/58
[52] U.S. Cl. ........................................................ 606/72
[58] Field of Search .............................. 606/69, 70, 71, 606/72, 73, 61, 60, 59, 54; 411/427

[56] References Cited

U.S. PATENT DOCUMENTS

| | | |
|---|---|---|
| 1,025,008 | 4/1912 | Miner . |
| 3,534,731 | 10/1970 | Muller . |
| 3,547,114 | 12/1970 | Haboush . |
| 3,596,656 | 8/1971 | Kaute . |
| 4,388,921 | 6/1983 | Sutter et al. . |
| 4,484,570 | 11/1984 | Sutter et al. . |
| 4,493,317 | 1/1985 | Klaue . |
| 4,692,290 | 9/1987 | Steffee . |
| 4,794,918 | 1/1989 | Wolter . |
| 4,828,441 | 5/1989 | Frasca ...................................... 411/427 |
| 4,867,144 | 9/1989 | Karas et al. . |
| 4,964,403 | 10/1990 | Karas et al. ............................... 606/60 |
| 5,013,313 | 5/1991 | Surer . |
| 5,041,113 | 8/1991 | Biedermann et al. ..................... 606/61 |
| 5,053,036 | 10/1991 | Perren et al. .............................. 606/69 |
| 5,057,111 | 10/1991 | Park .......................................... 606/69 |
| 5,090,854 | 2/1992 | Hafeli et al. ............................. 411/427 |
| 5,108,399 | 4/1992 | Eitenmuler et al. ...................... 606/77 |
| 5,127,914 | 7/1992 | Calderale et al. ........................ 606/65 |
| 5,129,899 | 7/1992 | Small et al. . |
| 5,147,363 | 9/1992 | Harle ........................................ 606/73 |
| 5,151,103 | 9/1992 | Tepic et al. ............................... 606/69 |
| 5,209,751 | 5/1993 | Farris et al. .............................. 606/61 |
| 5,234,431 | 8/1993 | Keller ....................................... 606/70 |
| 5,269,784 | 12/1993 | Mast ......................................... 606/69 |
| 5,618,144 | 4/1997 | Leistner ................................. 411/427 |

FOREIGN PATENT DOCUMENTS

| | | |
|---|---|---|
| 2254298 | 7/1975 | France . |
| 2499400 | 8/1992 | France . |
| 2266246 | 10/1993 | United Kingdom . |

*Primary Examiner*—Michael Buiz
*Assistant Examiner*—Vy Quang Bui
*Attorney, Agent, or Firm*—Fish & Richardson P.C.

[57] ABSTRACT

A threaded insert is designed to snap into a standard bone plate hole. The insert has an upper section divided into sectors by slots, a lower section having deflectable tabs with external projections, and a central threaded hole. When a standard bone screw is tightened in the insert, the insert rigidly fixes the screw to the plate by collapsing the threads of the insert onto the threads of the screw, and by expanding the sectors of the upper section to clamp the bone plate.

25 Claims, 6 Drawing Sheets

THREADED INSERT FOR BONE PLATE SCREW HOLE

FIELD OF THE INVENTION

The invention relates generally to threaded inserts for the rigid fixation of bone screws to bone plates having plate holes. The insert is adapted to be introduced into the plate hole, and to anchor the bone screw to the plate.

BACKGROUND OF THE INVENTION

In orthopaedics, stable fixation is a prerequisite for successful treatment of complex deformity, nonunion, and fracture. Bone plates are commonly used to obtain fixation and are commonly secured to the bone by screws. However, osteoporotic bone or bone with abnormally thinned cortices due to failed fixation or previous infection may not allow lasting screw purchase in the bone. Stability of the fractured bone gained by applying compression across the fracture site is quickly lost as the thin bone resorbs around the screws. This loss of compression is rapid, since loosening of the screws in the bone allows early toggling at the plate/screw interface.

As noted, most bone plates used in osteosynthesis are fixed solely by means of bone screws driven into the bone. Since the bone screws are only secured to bone, there is no rigid fixation of the screw to the bone plate. Therefore a loosening of the bone screws in the bone or a resorption of the bone can easily lead to a loosening of the bone plate.

It is known in plate osteosynthesis to use a nut on the cortex opposite a plate to fix the screw, and therefore the plate, to the bone. This method does not produce a direct fixation between bone screws and plate, but only compression of the bone located between the nut and the plate and penetrated by the screw.

In a variety of indications it is desirable to achieve a rigid fixation between bone screws and a bone plate in order to avoid subsequent loosening. For this purpose U.S. Pat. No. 5,053,036 teaches anchoring by frictional adhesion alone a bone screw with a specially designed conical head to a bone plate having corresponding conical holes. In this device both holes and screw heads must have a specific taper to obtain rigid fixation between them.

In U.S. Pat. No. 4,388,921, a bone screw with a specially designed conical or convex head is used in conjunction with a slotted insert having a matching tapered hole for the screw head. The special bone plate for use with this insert has cylindrical or spherical holes for the inserts. Because the insert is not threaded to receive the bone screw, fixation of the bone screw in the bone plate is dependent on the purchase of the bone screw threads in the bone.

U.S. Pat. No. 5,053,036 discloses a bone screw with a specially designed conical head used in conjunction with a slotted spherical insert in a bone plate. This design also requires the conforming tapers discussed above and in addition requires conforming spherical surfaces on the slotted sphere and in the bone plate.

Threaded conical inserts have been used to expand specially designed screw heads in order to lock the bone plate to the bone screw. Examples of this technique are found in U.S. Pat. Nos. 5,053,036 and 4,484,570. This design also requires conforming tapers on specially designed screws and plates.

U.S. Pat. No. 5,269,784 describes a nut interposed between the plate and the bone surface so that the plate is compressed between the head of the bone screw and the nut. An unthreaded bushing may be required in this arrangement between the screw head and the plate if the bone screw has an unthreaded portion near the head. Because the screw nut is installed on the underside of the bone plate, is must be introduced into the plate hole before or during operative placement of the bone plate. The nut must furthermore be retained in the plate by separate means during placement of the plate on the bone.

SUMMARY OF THE INVENTION

It is an object of the present invention to provide a means for locking a bone screw to a bone plate at a fixed angle, using standard bone screws and standard bone plates.

It is a further object to provide an insert for locking a bone screw to a bone plate wherein the insert need not be installed before the plate is placed on the bone.

It is a further object of the invention to provide a locking means for bone screws that does not require precision machining of matching tapers or matching spherical surfaces.

It is a further object of the invention to provide an insert for locking a bone screw to a bone plate wherein the locking function of the insert is not dependent on the purchase of the bone screw in the bone.

It is a further object of the invention to provide a locking insert for bone plates that can be snapped into the plate hole and will remain there until snapped out.

It is a further object of the invention to provide a locking insert for a bone screw that has a central hole inclined at an angle other than 90 degrees for use with a buttress plate.

In accordance with the invention, the noted drawbacks of the existing means of attaching bone screws to plates are overcome by an insert having an upper section and a lower section, a central axis extending through both sections, and a central hole extending along the axis through the insert. The central hole is threaded to engage a bone screw at least where the hole extends through the bottom section of the insert.

The lower section of the insert has slots dividing it into a plurality of tabs, each tab having an external projection. The distance between opposite projections is larger than a corresponding diameter of the plate hole opening. The tabs can be deflected to permit insertion of the external projections through the plate hole opening. Because the tabs must be similarly deflected in order to remove the insert from the plate hole, the insert will remain in place unless pressed out of the plate hole. When a bone screw is engaged in the threaded part of the central hole, the tabs can no longer be deflected and the insert cannot be removed from the plate hole.

The upper section of the insert has a cross sectional area larger than the plate hole, a downwardly facing locking shoulder for contacting the upper edge of the plate hole, and a countersunk surface for receiving the head of the bone screw. Slots divide the upper section into a plurality of sectors.

The insert can be pressed into a plate hole in the bone plate either before or after the plate is installed on the bone. When the bone screw is installed and tightened, the head of the screw contacts the countersunk surface of the insert, causing the sectors of the upper section to spread, clamping the bone plate between the downwardly facing locking surface and the external projections. The threads in the lower section collapse under the resultant forces, thereby preventing the bone screw from backing out.

In one embodiment of the invention, the external shape of the insert is configured for an elongated plate hole. This shape prevents the insert from rotating as the bone screw is driven. In an alternative embodiment, an insert may have an external shape for use in a round plate hole. In this case, a special wrench or other instrument may be used to prevent rotation of the insert while driving the screw.

In a further embodiment of the invention, an insert designed for use in round plate holes has a central hole disposed at an angle to the central axis and oriented at an angle other than 90 degrees to the bone plate. The insert can thereby be rotated prior to locking, enabling the user to aim the screw at any position along the cone formed by rotating the axis of the central hole of the insert around the plate hole. This feature is useful in buttress plates where the orientation of the screw must be adjusted.

One advantage of the threaded insert according to the invention resides in its universal applicability, since it can be used together with standard bone plates and screws. The insert can be used advantageously, for example, with the bone plate described in U.S. Pat. No. 4,493,317 to Klaue.

Inserts according to the invention can be installed individually at selected positions on a bone plate, while using standard bone screws without inserts at other locations. Because the inserts are installed in the bone plate from the side opposite the bone, it is possible to install the inserts after the bone plate has been placed on the bone. It is therefore possible to postpone deciding where to use the inserts until after the bone plate is in place, during the operation.

In a standard bone plate mounting, cycled loads will cause the screw to back out. Forces coaxial to the screw shaft cause the screw to loosen due to the effect of loading the inclined plane of the threads. This problem is magnified when the fragment is not fixed securely to the plate because of toggle occurring at the plate/screw interface. The threaded insert of the invention prevents the bone screw from backing out by collapsing and locking the threads of the insert on the screw. The insert also prevents toggling by holding the screw at a fixed angle with respect to the plate.

The insert of the invention is locked within the bone plate hole by compressive forces generated between the screw head and that portion of the screw threads engaged by the insert. Because the locking forces are contained completely within the insert, the insert remains locked in the bone plate hole independent of any degradation of bone screw purchase caused by mechanical or biological factors.

When tightened, the screw is secured to the plate in a fixed, usually orthogonal position, similar to the situation that is present when a pin is clamped to an external fixation frame. With the screw(s) thus fixed to the plate and bone, several advantages become evident. Firstly, in osteoporotic bone or bone with thin cortices, early loosening due to cycled loads is avoided, since the screws are fixed to the plate, rendering them exempt from the effects of toggling at the plate/screw interface.

Secondly, the insert acts as a mechanical cortex substitute in situations where bone is lost at the near cortex due to trauma or disease. Once the bone screw is locked by the insert, any bone fragment held by the bone screw will be fixed in space, since toggle of the screw with the plate will be eliminated. Therefore, if the bone is deficient adjacent to the bone plate, the surgeon can still place a screw through the opposite cortex, allowing fixation to be distributed over a greater portion of the plate.

Thirdly, the insert allows the bone screw to store some of the energy that is used when generating compression at a fracture or osteotomy site. This provides compression that lasts longer than that provided by a plate with screws, since cycled loads can lead to loosening. This effect is analogous to the preload and compression that is achieved with a ninety degree blade plate.

Finally, by using the insert, a surgeon can convert any portion of a plate into a "fixed pin" device, increasing the plate's versatility as an internal fixation device. When a surgeon wishes to immobilize bone fragments located at a distance from the plate, the insert can be used to prevent toggle at the plate/screw interface, increasing overall stability. The insert rigidly fixes the screw so that the bone fragment is held in a more restrained manner. This effect has been loosely termed the "locked lag technique".

BRIEF DESCRIPTION OF THE DRAWINGS

The invention will be disclosed more fully in connection with the accompanying drawings in which.

DETAILED DESCRIPTION

Figure 1:
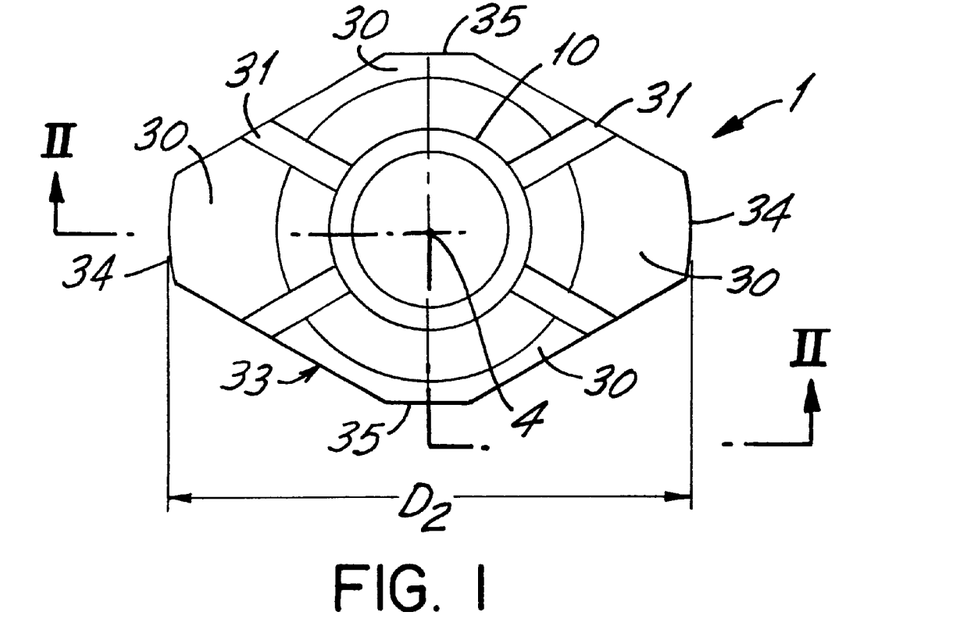
FIG. 1 is a top view of a threaded insert according to the invention for use in an elongated plate hole.
Figure 2:
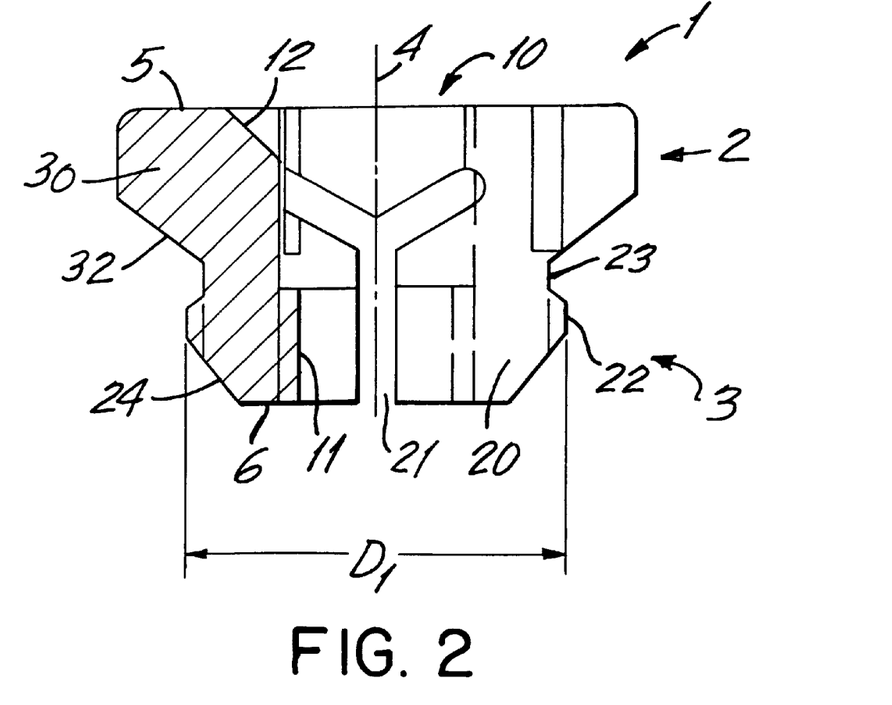
FIG. 2 is a side elevation view in partial cross section along the lines II—II of FIG. 1.

The threaded insert comprises an elongated body as shown in FIGS. 1 and 2, usually of metal such as stainless steel, or titanium or other biocompatible material. As best seen in FIG. 2, the insert 1 has a top section 2, a bottom section 3, a top surface 5, and a bottom surface 6. A central axis 4 extends through the top section 2 and the bottom section 3.

Extending along central axis 4 is central hole 10. The central hole 10 has threads 11 for receiving a bone screw (not shown). In the embodiment of FIG. 2 there are threads only in lower section 3, although the central hole in the upper section 2 can also be threaded. Central hole 10 has at the top surface 5 a countersunk surface 12 for contact with the underside of a bone screw head (not shown). Where the underside of a bone screw head is spherical, it has been found that an angle of the countersunk surface 12 of approximately 45 degrees to the central axis 4 works well in developing the necessary forces in the top section 2 as discussed below. Other angles may be used to accommodate other screw geometries or other limitations.

The bottom section 3 comprises a plurality of deflectable tabs 20 that extend downward from the top section 2. In the embodiment shown in FIG. 2, two tabs 20 are disposed so that they will be along a long diameter of the elongated plate hole (not shown), and are separated by Y-shaped slots 21. The Y-shaped configuration of the slots 21 reduces the cross-sectional area of the upper portion of the tabs 20, permitting greater deflection of the tabs as described below.

Each tab 20 comprises an external projection 22 protruding from its outer surface 23. A distance $D_1$ measured over the external projections 22 orthogonal to the central axis 4 of the insert is slightly larger than a corresponding distance across the long diameter of the elongated plate hole in which the insert is to be seated.

Figure 3:
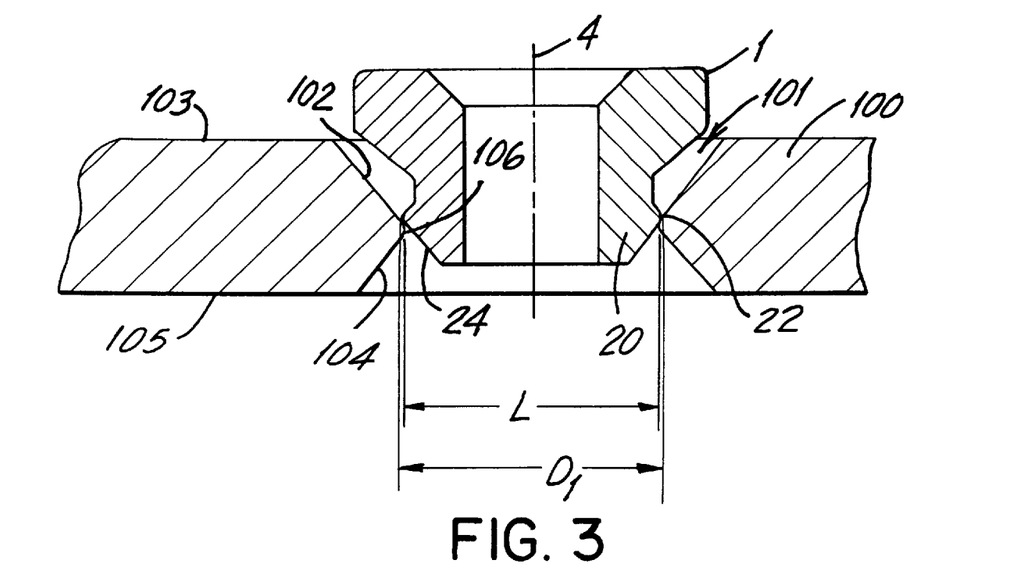
FIG. 3 is a view in vertical section of a threaded insert according to the invention in position to be assembled into a plate hole.

FIG. 3 shows insert 1 of FIGS. 1 and 2 in position to be assembled into plate hole 101 in plate 100. Projections 22 on tabs 20 are disposed along the long diameter of plate hole 101. The distance $D_1$ between the projections 22 is slightly larger than the distance L along the long axis of the plate hole. One skilled in the art will recognize that other configurations are possible. For example, where an odd number of tabs are to be used in a round plate hole, the inscribed circle through the projections 22 must be slightly larger than the diameter of the plate hole.

As best shown in FIG. 2, each tab 20 further comprises an external lead chamfer 24 on the bottom surface 6, adjacent the external projections 22. The chamfer 24 provides a camming surface for compressing the tabs 20 when the insert 1 is pressed into the plate hole 101, as described below.

The upper section 2 comprises a plurality of sectors 30 separated by slots 31 that extend down from the top surface 5 through the upper section 2. In the insert shown in FIG. 1, four sectors 30 are separated by two slots 31. The slots 31 in the upper section 2 are parallel to and pass through central axis 4.

Figure 4:
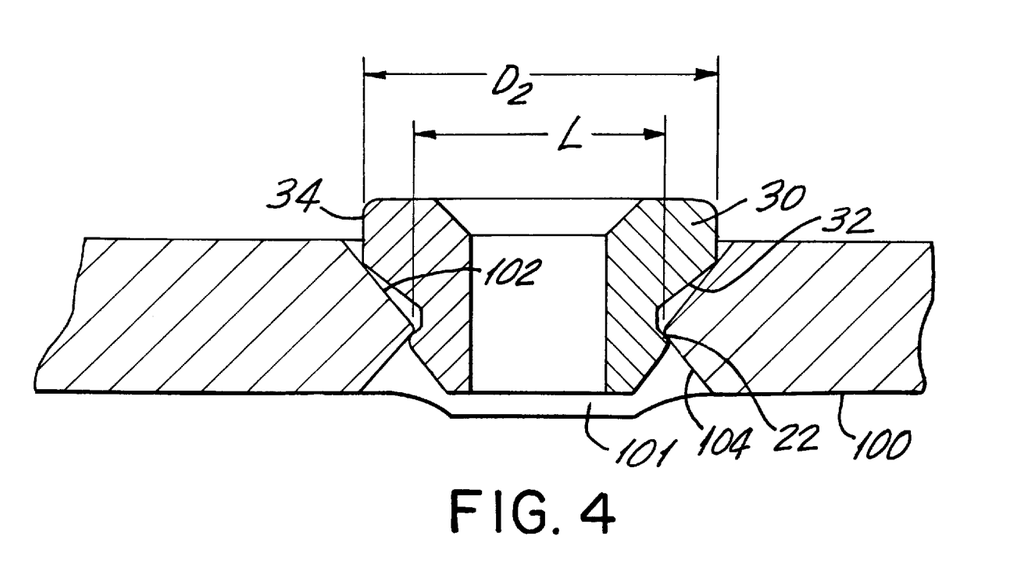
FIG. 4 is a view in vertical section of a threaded insert according to the invention positioned in a plate hole.

As best seen in FIG. 1, the upper section 2 has outside profile surfaces 34, 35, separated by flats 33. The distances between surfaces 34 and between surfaces 35 are larger than the corresponding diameters in the opening of the plate hole. For example, FIG. 4 shows an insert 1 that has been installed in a plate hole 101 in plate 100. The distance $D_2$ between outside profile surfaces 34, which lie on the long diameter of the plate hole 101, is larger than the distance L, the narrowest longitudinal dimension along the long diameter of the plate hole.

As best shown in FIG. 2, each sector 30 of the upper section 2 comprises a downward facing locking shoulder 32 adjacent to and facing the lower section 3. The locking shoulder 32 is disposed at an angle to the central axis 4, forming a convex, conical surface. The angle is selected to facilitate locking the insert in the plate, as described below.

FIGS. 3 through 6 illustrate the steps for installation of the insert of FIGS. 1 and 2. The bone plate hole 101 is of standard geometry, having a plate countersunk surface 102 extending from plate top surface 103, and an undercut chamfer 104 extending from the plate bottom surface 105. The intersection of the plate countersunk surface 102 and the undercut chamfer 104 forms lip 106, defining the opening of plate hole 101. Such a bone plate is described in U.S. Pat. No. 4,493,317, for example.

To install the insert 1 in a plate hole 101, the insert is introduced into the plate hole as shown in FIG. 3, with the central axis 4 of the insert coinciding with the center of the plate hole, and the lead chamfer 24 contacting the bone plate 100. More specifically, the insert lead chamfer 24 contacts the plate countersunk surface 102 of the plate hole 101.

The insert 1 is then pushed in the direction of the bone plate 100, whereupon plate countersunk surface 102 exerts a reaction force on lead chamfer 24. This force deflects tabs 20 inward, reducing distance $D_1$. The tabs bend at their upper portions, where the Y-shaped slots 21 have reduced the cross sectional area. When distance $D_1$ is sufficiently reduced by this deflection so that the projections 22 can pass through the opening defined by lip 106, the insert snaps into plate hole 101 in the position shown in FIG. 4. Projections 22 contact undercut chamfer 104 and slide outward and downward along this surface, pulling the insert into the plate hole 101 until the locking shoulder 32 contacts the plate countersunk surface 102. The insert 1 is thereby retained in the plate hole 101 by the projections 22 and the locking shoulder 32.

Figure 5:
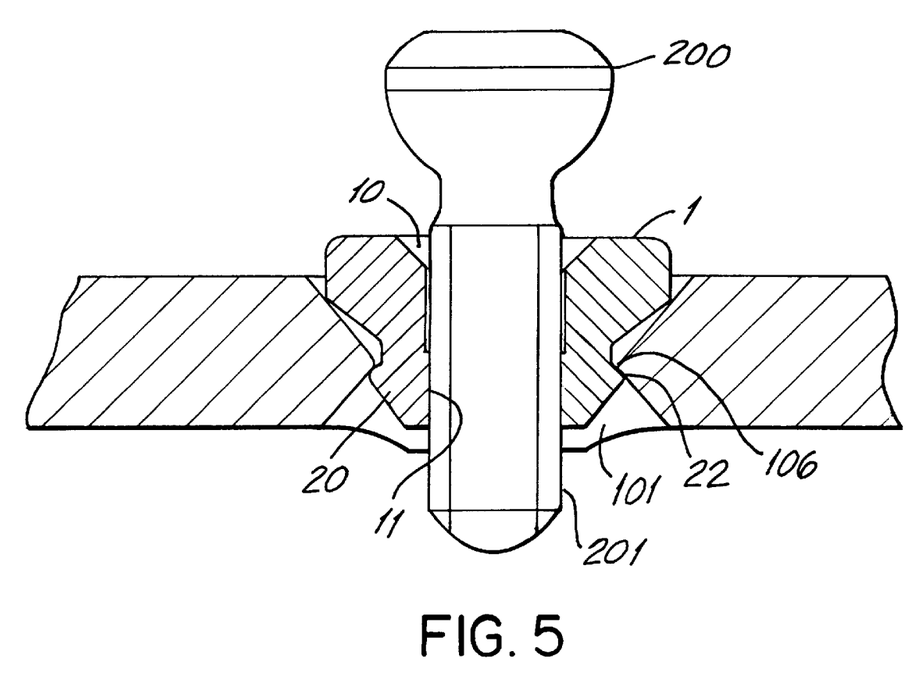
FIG. 5 is a view in vertical section of a threaded insert according to the invention partially positioned in a plate hole, and showing a bone screw partially positioned in the insert.

FIG. 5 shows the insert 1 in the plate hole 101 after a bone screw 200 has been partially threaded into the insert. External bone screw threads 201 engage threads 11 of central hole 10 in the region of tabs 20. This prevents tabs 20 from deflecting inward, locking tab projections 22 in position under bone plate lip 106, and preventing removal of the insert 1 from the bone plate hole 101.

Figure 6:
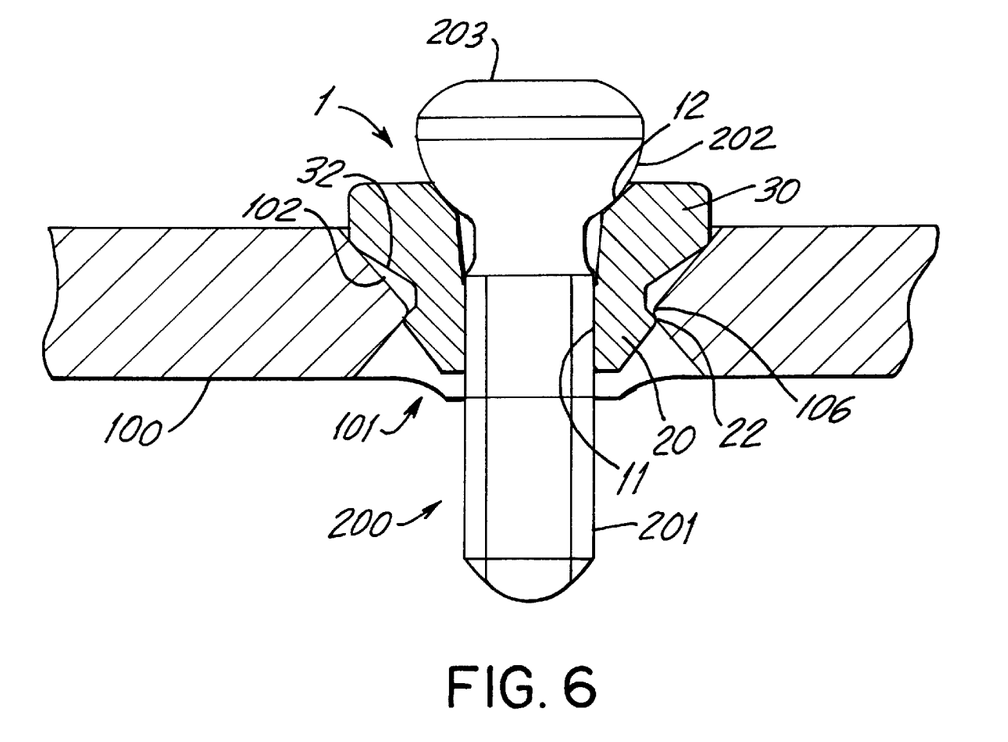
FIG. 6 is a view in vertical section of a fully assembled threaded insert, bone screw and bone plate according to FIG. 5.

FIG. 6 shows the insert 1, bone plate 100, and bone screw 200 after the bone screw has been fully tightened. The spherical underside 202 of the bone screw head 203 contacts the countersunk surface 12 of the insert, causing the sectors 30 of the insert to spread apart. This spreading of sectors 30 causes locking shoulder 32 to exert a force on the plate countersunk surface 102. The force causes a small displacement of insert 1 in an upward direction, causing forceful contact of the projections 22 with the underside of lip 106. The insert 1 is thereby locked in position in the plate hole 101.

The resultant force on projections 22 causes tabs 20 to be deflected slightly inward, collapsing threads 11 inward to forcibly engage bone screw threads 201. The forcible thread engagement locks bone screw 200 against loosening by rotation.

Figure 7:
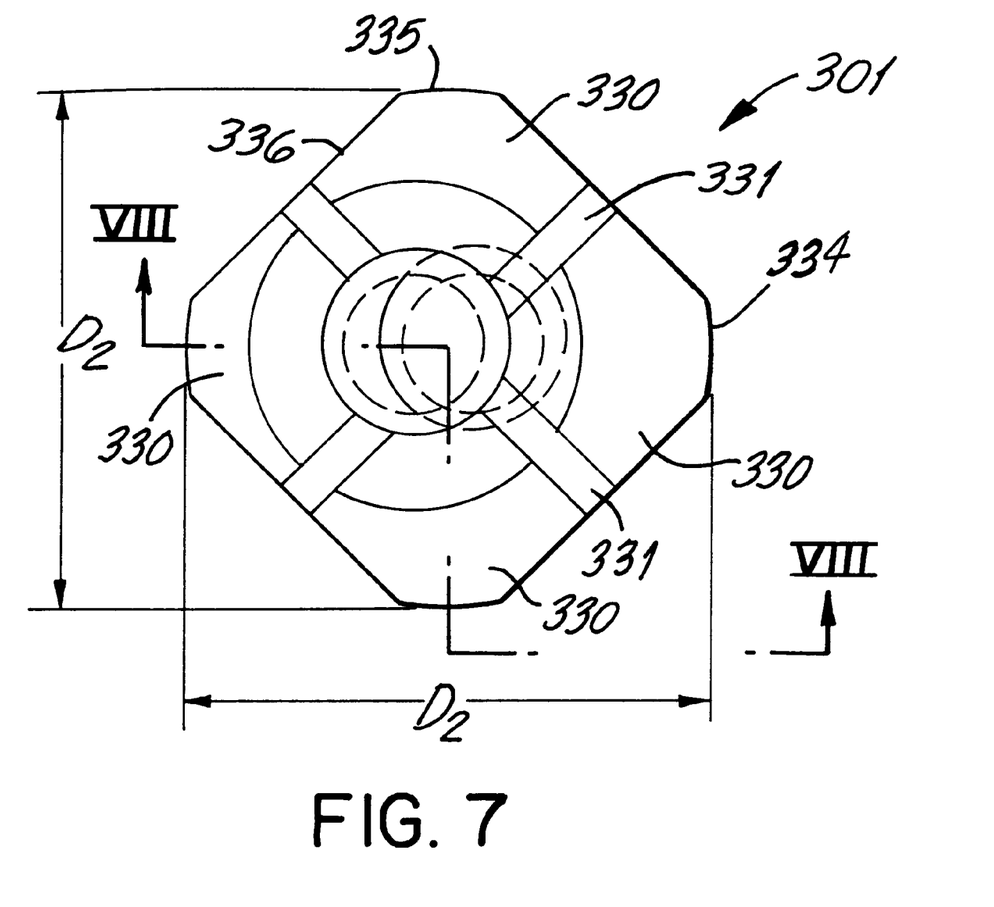
FIG. 7 is a top plan view of a threaded insert according to the invention for use in a round plate hole, in which the central hole is inclined at an angle other than 90 degrees to the plane of the bone plate.
Figure 8:
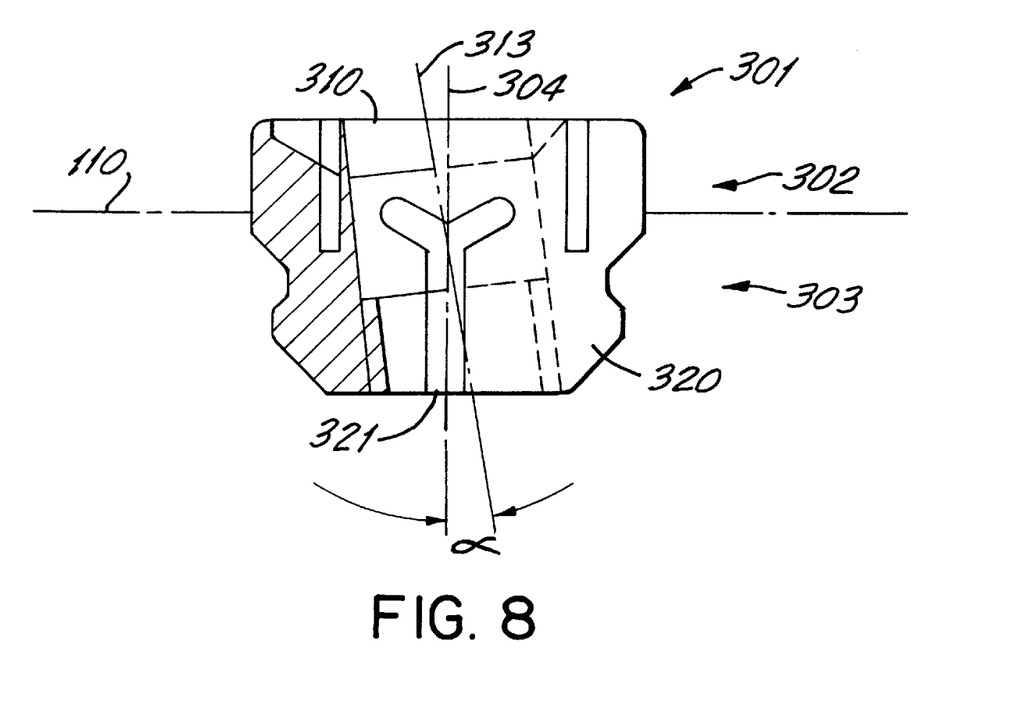
FIG. 8 is a side elevation view in partial cross section along lines VIII—VIII of FIG. 7.

FIGS. 7 and 8 show an embodiment of the invention with an angled screw hole for use in applications such as buttress plates. As best shown in FIG. 8, insert 301 has a top section 302, a bottom section 303, a central axis 304, and a partially threaded central hole 310. Bottom section 303 comprises a plurality of deflectable tabs 320 separated by Y-shaped slots 321.

As best seen in FIG. 7, the upper section 302 comprises four sectors 330 separated by two slots 331. Distance $D_2$ is the same between both pairs of outside profile surfaces 334, 335 because the insert 301 is to be used in a round plate hole. Because the insert is used in a round hole, provision for preventing rotation, such as wrench flats or the like (not shown), must be made for use when the screw is driven.

Central hole 310 of insert 301 is inclined at an angle other than 90 degrees to the bone plate plane 110. As shown in FIG. 8, central hole axis 313 is inclined at angle α to the central axis 304. A bone screw (not shown) engaged in central hole 310 of insert 301 is therefore inclined at an angle other than 90 degrees to the bone plate. The direction of inclination of the bone screw can be changed by rotating insert 301 in the bone plate hole, thereby aiming the screw in any position on a cone formed by rotating axis 313 around axis 304. This embodiment of the invention is particularly useful in buttress plates where the fixed angle of the screw must be adjusted.

What is claimed is:

1. A one piece locking insert for connecting a bone screw to a bone plate having at least one hole with an angled lower surface, the insert comprising upper and lower sections, and a central screw hole through said upper and lower sections, said central screw hole being threaded in at least said lower section, said upper section having an upwardly facing surface for engaging a bone screw head, and a downward facing locking surface for contacting a top edge of the bone plate hole, and said lower section having retaining means for contacting the angled lower surface of the bone plate hole.

2. The insert of claim 1, further comprising a central axis through said upper section and said lower section, said locking surface having a cross section in a plane normal to said central axis wherein the width of said cross section is smaller than the length of said cross section.

3. The insert of claim 2, wherein said central screw hole is disposed along said central axis.

4. The insert of claim 1, further comprising a central axis through said upper section and said lower section, said locking surface having a cross section in a plane normal to said central axis wherein a width of said cross section is equal to a length of said cross section.

5. The insert of claim 4, wherein said central screw hole is disposed along said central axis.

6. The insert of claim 4, wherein said central screw hole is disposed at an angle to said central axis.

7. The insert of claim 1 wherein said screw hole is threaded in both said upper and lower sections.

8. The insert of claim 1 wherein the upper section is divided into a plurality of sectors by slots extending from said upwardly facing surface.

9. A one piece locking insert for connecting a bone screw to a bone plate having at least one hole with angled upper and lower surfaces, the insert comprising an upper section, a lower section and a central screw hole through said upper and lower sections, said hole being threaded in at least said lower section, said upper section being divided into a plurality of expandable sectors by a plurality of slots, said sectors having upwardly facing surfaces for engaging a bone screw head, and downwardly facing locking surfaces for contacting the angled upper surface of the bone plate hole, and said lower section having retaining means for contacting the angled lower surface of the bone plate hole.

10. The insert of claim 9 herein said screw hole is threaded in both said upper and lower sections.

11. A locking insert for connecting a bone screw to a bone plate having at least one hole with an angled lower surface, the insert comprising an upper section, a lower section and a central screw hole through said upper and lower sections, said central screw hole being threaded in at least said lower section, said upper section having an upwardly facing surface for engaging a bone screw head, and a downward facing locking surface for contacting a top edge of the bone plate hole, and said lower section having a compressible structure, and at least one projection for contacting the angled lower surface of the bone plate hole.

12. The insert of claim 11, wherein said compressible structure comprises at least one deflectable tab supporting said at least one projection.

13. The insert of claim 12, wherein said threads of said central screw hole are provided for locking said deflectable tabs when the bone screw is threaded into said central screw hole.

14. The insert of claim 11, wherein said at least one projection retains the insert in the bone plate hole by exerting a force on said angled lower surface.

15. The insert of claim 11 wherein said screw hole is threaded in both said upper and lower sections.

16. An assembly for internal fixation of bones comprising a bone plate having a plate hole with an upward facing countersunk surface and a downward facing undercut chamfer, in combination with a one piece insert for fixing a bone screw in said plate hole, said insert comprising a central threaded hole for the bone screw, a locking surface for clamping over said countersunk surface and a projection for engagement with said undercut chamfer.

17. The assembly of claim 16, wherein said locking surface comprises downwardly-facing surfaces of a plurality of expandable sectors.

18. The assembly of claim 16, wherein said projection depends from an outer surface of a deflectable tab.

19. The assembly of claim 18, wherein the bone screw contacts an inside surface of said deflectable tab, locking said deflectable tab in a radially outward position.

20. An assembly for internal fixation of a bone comprising a bone plate having a plate hole with an upward facing countersunk surface and a downward facing undercut chamfer, in combination with a one piece insert for connecting a bone screw to said plate, said insert comprising an upper section, a lower section and a central screw hole through said upper and lower sections, said hole being threaded in at least said lower section, said upper section having an upwardly facing surface for engaging a bone screw head and a downwardly facing locking surface for contacting the upward facing countersunk surface of said bone plate hole.

21. The assembly of claim 16 wherein said screw hole is threaded in both said upper and lower sections.

22. An assembly for internal fixation of bones comprising
a bone plate having at least one plate hole between the outer surface and the inner, bone-contacting surface, said plate hole having a smaller diameter in a section between said surfaces that at either surface,
a one-piece, locking insert for connecting a bone screw to said plate, said insert comprising an upper section engaging said plate in said hole above its smaller dimension, a lower section capable of passing through said smaller diameter section of said plate hole and engaging said plate in said hole below its smaller dimension and a central hole through said upper and lower sections, said central hole being threaded in at least said lower section, and
a threaded bone screw passing through said central hole, engaging the threaded portion of said central hole and pressing said insert against said plate above the smaller diameter section in said plate hole.

23. The assembly of claim 22 wherein said lower portion of the insert is wholly within said plate hole.

24. The assembly of claim 20 wherein said lower portion of the insert is wholly within said plate hole.

25. A one piece, locking insert for connecting a bone screw to a bone plate having at least one plate hole between the outer surface and the inner, bone-contacting surface, said plate hole having a smaller diameter in a section between said surfaces than at either surface,
said one piece insert comprising an upper section for engaging said plate in said hole above its smaller dimension, a lower section capable of passing through said smaller diameter section of said plate hole and engaging said plate in said hole below its smaller dimension and a central hole through said upper and lower sections, said central hole being threaded in at least said lower section for engaging a threaded bone screw passing through said central hole and pressing said insert against said plate above the smaller diameter section in said plate hole.

* * * * *

(12) EX PARTE REEXAMINATION CERTIFICATE (8180th)
United States Patent
Haag et al.

(10) Number: US 5,976,141 C1
(45) Certificate Issued: Apr. 26, 2011

(54) THREADED INSERT FOR BONE PLATE SCREW HOLE

(75) Inventors: Rene Haag, Devon, PA (US); Michael H. Mackin, Exton, PA (US); Jeffrey W. Mast, Gross Pointe Park, MI (US); Timothy M. Chadwick, Downingtown, PA (US)

(73) Assignee: Synthes (U.S.A.), Paoli, PA (US)

Reexamination Request:
No. 90/009,327, Dec. 17, 2008

Reexamination Certificate for:
Patent No.: 5,976,141
Issued: Nov. 2, 1999
Appl. No.: 08/392,540
Filed: Feb. 23, 1995

(51) Int. Cl.
*A61B 17/80* (2006.01)
*A61B 17/68* (2006.01)
*A61B 17/86* (2006.01)
*A61B 17/58* (2006.01)

(52) U.S. Cl. ................................ 606/292; 606/301
(58) Field of Classification Search .................. None
See application file for complete search history.

(56) References Cited

U.S. PATENT DOCUMENTS

| | | | |
|---|---|---|---|
| 1,150,114 A | | 8/1915 | Hays |
| 2,393,606 A | * | 1/1946 | Brush ........................ 411/80.1 |
| 2,612,073 A | | 9/1952 | Taylor |
| 2,785,726 A | * | 3/1957 | Brush ........................... 411/16 |
| 3,449,799 A | * | 6/1969 | Bien ........................... 411/548 |
| 3,566,947 A | | 3/1971 | Jukes |
| 4,325,665 A | | 4/1982 | Winchell |
| 4,352,589 A | | 10/1982 | Allison et al. |
| 4,388,921 A | | 6/1983 | Sutter et al. .................. 606/71 |
| 4,484,570 A | | 11/1984 | Sutter et al. |
| 4,493,317 A | | 1/1985 | Klaue |
| 4,657,458 A | | 4/1987 | Wollar et al. |
| 4,776,330 A | | 10/1988 | Chapman et al. |
| 4,952,107 A | | 8/1990 | Dupree |
| 5,053,036 A | | 10/1991 | Perren et al. |
| 5,065,490 A | | 11/1991 | Wivagg et al. |
| 5,151,103 A | | 9/1992 | Tepic et al. |
| 5,269,784 A | | 12/1993 | Mast ........................... 606/69 |
| 5,330,535 A | | 7/1994 | Moser et al. |
| 5,645,606 A | | 7/1997 | Oehy et al. |
| 5,741,258 A | | 4/1998 | Klaue et al. |

FOREIGN PATENT DOCUMENTS

| | | |
|---|---|---|
| FR | 2674118 | 9/1992 |
| GB | 2266246 | 10/1993 |
| WO | WO/94/016634 | 3/2004 |

OTHER PUBLICATIONS

Fasteners Handbook by Julius Soled, P.E. Consulting EngineerCopyright, 1957, p. 43.
Declaration of William L. Mentlik In Support of Howmedica's Responsive Claim Construction Brief (Jan. 16, 2008).
Synthes' Reply Claim Construction Brief (Jan. 28, 2008).
Declaration of Matthew S. Jorgenson re Claim Construction (with attached exhibit) (Mar. 13, 2008).
Expert Report of Dr. Marta Villarraga (with attached exhibits) (Aug. 22, 2008).
Ryan et al., Bolt–plate fixation for anterior spinal fusion, Clin Orthop (203): pp. 196–202, 1986.
Steffee et al., Segmental spine plates with pedicle screw fixation, Clin Orthop (203): pp. 45–53, 1986.

(Continued)

*Primary Examiner*—David O. Reip (57) ABSTRACT

A threaded insert is designed to snap into a standard bone plate hole. The insert has an upper section divided into sectors by slots, a lower section having deflectable tabs with external projections, and a central threaded hole. When a standard bone screw is tightened in the insert, the insert rigidly fixes the screw to the plate by collapsing the threads of the insert onto the threads of the screw, and by expanding the sectors of the upper section to clamp the bone plate.

OTHER PUBLICATIONS

Steffee and Sitkowski, Posterior lumbar interbody fusion and plates, Clin Orthop (227): pp. 99–102 (1988).
Ramotowski and Granowski, Zespol: An original method of stable osteosynthesis, Clin Orthop (272):pp. 67–75, 1991.
Deposition transcript of Dr. Marta Villararga (Oct. 14, 2008).
Rebuttal Expert Report of Dr. Wilson Hayes (with attached exhibits; redacted) (Sep. 30, 2008).
Deposition transcript of Dr. Wilson Hayes (Oct. 15, 2008).
Howmedica's Motion for Partial Modification of Scheduling Order (Sep. 19, 2008).
Howmedica's Memorandum in Support of Their Motion for Partial Modification of Scheduling Order (Sep. 19, 2008).
Declaration of Gregg A. Paradise (with attached exhibits) (Sep. 19, 2008).
Synthes' Opposition to Howmedica's Motion for Partial Modification of Scheduling Order (Oct. 3, 2008).
Declaration of Matthew S. Jorgenson In Support of Synthes' Opposition to Howmedica's Motion for partial modification of scheduling order (Oct. 3, 2008).
Howmedica's Reply Memorandum in Further Support of Its Motion for Partial Modification of Scheduling Order (Oct. 15, 2008).
Reply Declaration of Gregg A. Paradise (with attached exhibit) (Oct. 24, 2008).
Order of Partial Modification of Scheduling Order by Judge Anita Brody (Nov. 24, 2008).
Motion by Howmedica for Leave to Amend and Supplement Its Answer (Feb. 26, 2009).
Memorandum of Howmedica in Support of its Motion for Leave to Amed and Supplement Its Answer (Feb. 26, 2008).
Declaration of Gregg A. Paradise in Support of Motion by Howmedica for Leave to Amed and Supplement its answer (Feb. 26, 2009).
Synthes' Opposition to Howmedica's Motion for Leave to Amend and Supplement Its Answer (Mar. 3, 2008).
Declaration of Rene Regarding the Date of Completion, and Actual Reduction to Practice of the invention of U.S. Patent No. 5,976,141 (Mar. 19, 2009).
Declaration of Paul H. Meier (with attached exhibits) (Mar. 19, 2009).
File History of U.S. Patent No. 5,741,258.
Email from Gregg Paradise (attorney for Howmedica) to Jeffrey M. Olson (attorney for Synthes) (Nov. 14, 2008).
Howmedica—your orthopaedic resource—"1990 Product Catalog".
"Stryker"—"Surgical Techniques—Alta® Lag Screw Surgical Technique" by Michael W. Chapman M.D. and Dana C. Mears, M.D. Ph.D. (no date).
Howmedica photographs ("bone plate and insert" per Howmedica).
Howmedica "Alta Modular Trauma System" documents.
"Howmedica Surgical Techniques—Alta Lag Screw Surgical Technique" by Michael W. Chapman, M.D. and Dana C. Mears, M.D., Ph.D. (no date).
"Howmedica—your orthopaedic resource"—"1993 Product Catalog".
Rao et al., Clinical Evaluation of the Alta Hip Bolt in Peritrochanteric Hip Fractures, The American Journal of Orthopedics, Sep. 1998, pp. 612–616.
Cover page of Journal of Orthopaedic Trauma, vol. 6, No. 1, 1992 and a page which appears to be advertisment for the Alta Modular Trauma System (no date).
"Alta Modular Trauma System—The Howmedica Alta Hip Bolt Surgical Technique" by Michael W. Chapman, M.D., Dana C. Mers, M.D., Ph.D., and Charles C. Edwars, M.D. (no date).
Howmedica Surgical Techniques—"Digital Femoral Plating Surgical Technique" by Dana C. Mears M.D., PH.D. (no date).
"Howmedica 1997/8 Product Catalog".
Order Staying Civil Action No. 06 5681 AB ("Pennsylvania Action") by Judge Anita Brody (Mar. 19, 2009).
Order on Claim Construction (U.S. Patent No. 5,976,141) in Pennsylvania Action by Judge Anita Brody (Mar. 24, 2008).
Docket sheet for Pennsylvania Action (as of Apr. 21, 2009).
Howmedica's Preliminary Invalidity Contentions (Sep. 25, 2007).
Synthes' Opening Claim Construction Brief (Dec. 28, 2007).
Howmedica's Responsive Claim Construction Brief (Jan. 16, 2008).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2, 3, 16 and 18-24 is confirmed.

Claims 1, 4-6, 11 and 25 are cancelled.
Claims 7, 12, 14 and 15 are determined to be patentable as amended.
Claim 13, dependent on an amended claim, is determined to be patentable.
Claims 8-10 and 17 were not reexamined.

7. The insert of claim [1] *2* wherein said screw hole is threaded in both said upper and lower sections.

12. The insert of claim 11, wherein said compressible structure comprises at least one deflectable tab supporting said at least one projection, *and further comprising a central axis through said upper section and said lower section, said locking surface having a cross section in a plane normal to said central axis wherein the width of said cross section is smaller than the length of said cross section.*

14. The insert of claim 11, wherein said at least one projection retains the insert in the bone plate hole by exerting a force on said angled lower surface *and further comprising a central axis through said upper section and said lower section, said locking surface having a cross section in a plane normal to said central axis wherein the width of said cross section is smaller than the length of said cross section.*

15. The insert of claim 11 wherein said screw hole is threaded in both said upper and lower sections *and further comprising a central axis through said upper section and said lower section, said locking surface having a cross section in a plane normal said central axis wherein the width of said cross section is smaller than the length of said cross section.*

* * * * *